United States Patent [19]
Keown

[11] Patent Number: 5,667,521
[45] Date of Patent: Sep. 16, 1997

[54] RAPID EXCHANGE CATHETER

[75] Inventor: Kenneth Keown, San Diego, Calif.

[73] Assignee: Medtronic, Inc., Minneapolis, Minn.

[21] Appl. No.: 591,252

[22] Filed: Jan. 19, 1996

Related U.S. Application Data

[63] Continuation of Ser. No. 324,187, Oct. 4, 1994, abandoned, which is a continuation of Ser. No. 975,456, Nov. 12, 1992, Pat. No. 5,383,853.

[51] Int. Cl.[6] ............................................. A61M 29/00
[52] U.S. Cl. ......................................................... 606/194
[58] Field of Search ..................... 604/96, 101; 606/191, 606/192, 194

[56] References Cited

U.S. PATENT DOCUMENTS

| | | | |
|---|---|---|---|
| 4,748,982 | 6/1988 | Horzewski | 128/344 |
| 4,762,129 | 8/1988 | Bonzel | 128/344 |
| 4,771,777 | 9/1988 | Horzewski | 128/344 |
| 4,824,435 | 4/1989 | Giesy et al. | 604/49 |
| 4,988,356 | 1/1991 | Crittenden | 606/192 |
| 5,024,234 | 6/1991 | Leary et al. | 128/344 |
| 5,040,548 | 8/1991 | Yock | 128/898 |
| 5,046,497 | 9/1991 | Millar | 128/637 |
| 5,061,273 | 10/1991 | Yock | 606/194 |
| 5,324,257 | 6/1994 | Osborne et al. | 604/53 |
| 5,395,332 | 3/1995 | Ressemann et al. | |

FOREIGN PATENT DOCUMENTS

| | | |
|---|---|---|
| 0380227 | 8/1990 | European Pat. Off. |
| 3934695 | 4/1991 | Germany |

OTHER PUBLICATIONS

"Balloon Catheters for Percutaneous Insertion into the Vascular System" by Bjorn Nordenstrom; Acta Radiol 57:411–416, Nov. 1962.

"New Instruments for Catheterization and Angiocardiography" by Bjorn Nordenstrom; Radiology, vol. 85, Jul.–Dec. 1965, pp. 256–259.

*Primary Examiner*—Corrine M. McDermott
*Attorney, Agent, or Firm*—Dianne M. F. Plunkett; Harold R. Patton

[57] ABSTRACT

The present invention relates to over-the-wire PTCA balloon catheters (5), and more particularly, to a rapid exchange catheter with the guidewire lumen (50) at the distal tip. The present invention discloses a rapid exchange medical catheter having a wire guiding means external to the shaft (35) for slidably mounting over the guidewire (55), the wire guiding means being a short tubular member having a proximal end and a distal end extending proximally from the distal end of the shaft (35) and terminating before the distal end of the balloon therapy means.

3 Claims, 6 Drawing Sheets

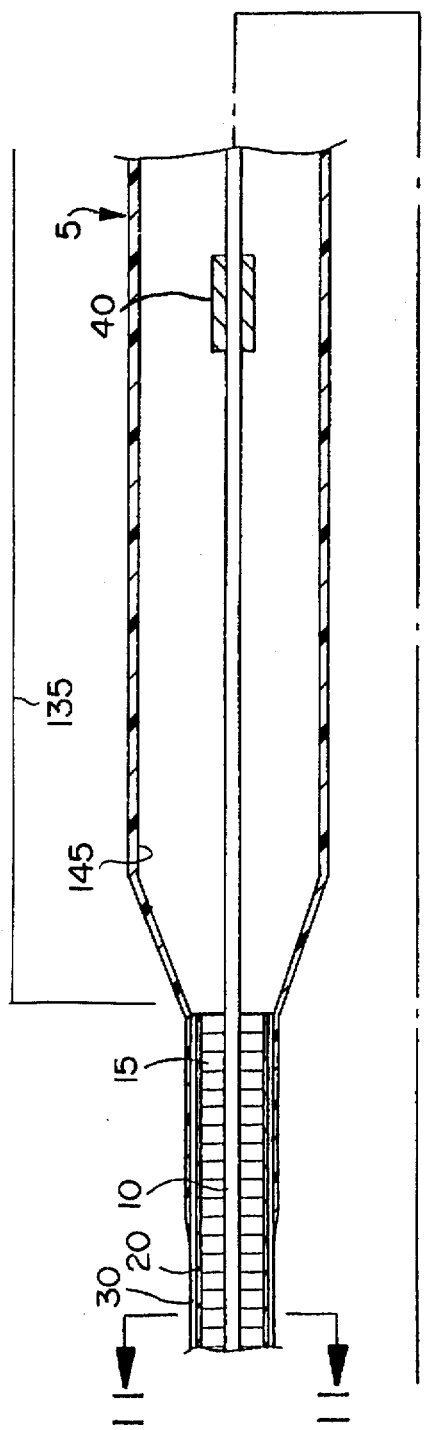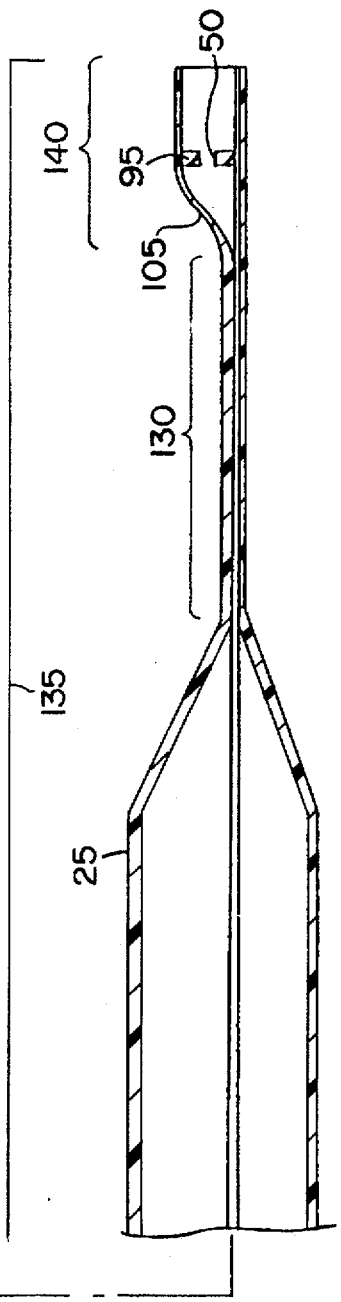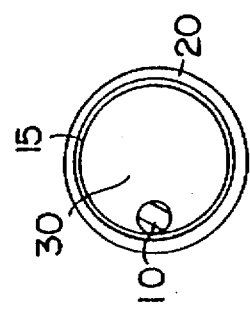
FIG. 10
FIG. 11

RAPID EXCHANGE CATHETER

This application is a continuation of application Ser. No. 08/324,187 filed on Oct. 4, 1994 now abandoned which is a continuation of U.S. patent application Ser. No. 07/975,456 filed Nov. 12, 1992 issued as U.S. Pat. No. 5,383,853.

FIELD OF THE INVENTION

The present invention relates to over-the-wire PTCA balloon catheters, and more particularly, to a rapid exchange catheter with the guidewire lumen at the distal tip.

DESCRIPTION OF THE PRIOR ART

This description of art is not intended to constitute an admission that any patent, publication or other information referred to is "prior art" with respect to this invention, unless specifically designated as such. In addition, this section should not be construed to mean that a search has been made or that no other pertinent information as defined in 37 C.F.R. §1.56(a) exists.

Catheters comprise tube-like members inserted into the body for diagnostic or therapeutic medical reasons. One of the therapeutic procedures applicable to the present invention is known as percutaneous transluminal coronary angioplasty (PTCA). PTCA has evolved through three major stages, fixed wire systems, over-the-wire systems and rapid exchange systems. The first PTCA procedure was developed in approximately 1976–1977 by Dr. Andreas Gruntzig. This fixed wire system featured a core or guidewire fixed within the catheter to stiffen it so that it could be pushed into position in the vascular system. Blockage in a coronary artery could be reduced by positioning the balloon dilatation catheter across from the blockage and inflating the balloon causing the blockage to decrease.

In 1980–1981, Dr. John Simpson began to modify the fixed wire system developing an over-the-wire catheter with a free central lumen for movable guide wires and with a dilatation balloon formed from the outer surface covering in a unitary, that is, one-piece construction. This catheter system is the subject of U.S. Pat. No. 4,323,071 assigned to Advanced Cardiovascular Systems, Inc. (ACS). Using such a movable wire system, one could more readily select the desired coronary artery and reach smaller branches as movable guide wires are inherently smaller and more flexible than the fixed wire systems.

If a catheter must be exchanged for one of a different size, the over-the-wire system is advantageous because the guidewire can be left in place. The catheter is withdrawn over the guidewire and another catheter slid into place over it. A disadvantage of this exchange procedure is that it is difficult to keep the guidewire in place, since removing the catheter requires removal of the guidewire and subsequent recrossing of the stenosis, or alternatively, the use of a very long "exchange" guidewire of approximately 300 cm which is difficult to handle. Such a procedure requires two operators who must be in communication during the procedure. This requires more time and risks contamination by dropping the guidewire from the sterile field. An alternative to these long exchange guidewires is a two-part guidewire. This is also undesirable because it requires additional time to assemble and may be too thick to allow smooth exchanges. Rapid exchange catheters were developed to respond to the disadvantage of the long "exchange" wire in over-the-wire systems. These catheters have shorter guidewire lumens so that the guidewire exits from the catheter closer to the balloon than to the proximal end of the catheter. This enables the physician to anchor or hold the guidewire as he or she removes the catheter from the body, the exchange occurring over the shorter guidewire lumen.

One of the first rapid exchange catheters in biaxial form is U.S. Pat. No. 4,762,129 issued to Bonzel. A disadvantage of this catheter is the position of the guidewire exit port at the proximal balloon bond coupled with a short guidewire exchange lumen which can cause the balloon to become snagged during withdrawal through the tortuous path. The resultant buckling of the catheter may result in inadvertent withdrawal of the guidewire from the lesion due to seizure of the guidewire by the buckled lumen.

Rapid exchange catheter designs such as those in Yock, U.S. Pat. Nos. 5,040,548 and 5,061,273, responded to the Bonzel catheter disadvantages by lengthening the guidewire exchange lumen. In Yock, the guidewire lumen passes through the balloon and is generally coaxial with respect to the inflation lumen, but exits (or enters) in the side port at least 10 centimeters from the distal tip of the catheter. The Yock disclosure suggests a lumen of 10 or more centimeters; in catheters on the market, the lumen varies from about 9 to 35 centimeters in length. The lengthened guidewire lumen, however, induces friction between the catheter and guidewire during catheter manipulation and withdrawal. Such friction can contribute to extraneous guidewire movement.

Other versions of rapid exchange catheters in biaxial form are shown in the following patents: U.S. Pat. No. 4,748,982 issued to Horzewski, et al., and U.S. Pat. No. 4,988,356 issued to Crittenden. Here the guidewire lumen contains a slit extending its length (except where it passes through the balloon) so that the guidewire can be removed from the lumen through the slit at a point immediately proximal to the balloon. These variants, too, have a lengthened guidewire lumen which induces friction between the catheter and guidewire during catheter manipulation and withdrawal. Such friction can contribute to extraneous guidewire movement.

German patent application P 39 34 695.1 to Rupprecht discloses a longitudinal slot 2 which extends up the central axis of the catheter reaching from any location on the catheter to the end of the catheter. The longitudinal slot allows the rapid exchange of the guidewire by guiding it up the central guide channel 3 throughout the entire length of the catheter.

Other art of interest includes balloon catheters such as that described by Björn Nordenström in *Acta radiol*, 57:411–416, November 1962. A flexible steel wire is introduced through the tip of the catheter and taken out through the side hole distal to the balloon (page 112 FIG. I type I and page 413 FIG. 2 type 2). Because the guide wire must be angled to exit the side hole the Nordenström guide wire will tend to get caught and be removed along with the catheter precluding exchanging catheters. The Nordenström catheter materials consist of teflon or opaque polythene material plus latex rubber balloons. (See page 412). Thus air bubbles are not visible during the purging process to alert the operator to malfunction. Furthermore, latex balloons do not have a known diameter at specific pressures and may expand beyond the size of the vessel.

An angiocardiographic balloon catheter is also described by Björn Nordenström in *RADIOLOGY*, 85:256–259, July-December 1965. Page 257, FIG. A depicts a relatively long tip through which the guidewire is passed to facilitate the injection of contrast medium. U.S. Pat. No. 4,824,435 to Giesy and U.S. Pat. No. 5,046,497 to Millar represent another variety of catheters, those for instrument delivery. Giesy discloses a method and apparatus for guiding diagnostic and therapeutic devices into tortuous body passages but not a second catheter or dilatation device. A secondary guidewire 12 or an obturator 42 has a guide loop 10 or lumen comprising a member which may be threaded over a primary guidewire 14. This allows passage of an instrument over the guidewire 14 without the use of a through-lumen. The guide loop 10 is positioned at the tip or distal end of the instrument. The instrument is advanced alongside the guide wire 14 and is kept on course via the secondary guide wire 12 pushing behind the instrument.

U.S. Pat. No. 5,046,497 to Millar discloses a coupling structure 20 slidably engaging the guidewire allowing a plurality of diagnostic or therapeutic catheters such as sensor-carrying catheters to be coupled to a common guidewire.

SUMMARY OF THE INVENTION

The present invention discloses a rapid exchange medical catheter having a wire guiding means external to the shaft for slidably mounting over the guidewire, the wire guiding means being a short tubular member having a proximal end and a distal end extending proximally from the distal end of the shaft and terminating before the distal end of the therapy means. The advantages of applicant's invention are first, only one operator is required for the procedure, second, an inner lumen is not required to accommodate the guidewire, third, a short exchange lumen results in less friction and a faster exchange, and fourth, pinching the guidewire is minimized as the catheter is being removed through the tortuous path thereby tending to minimize pulling out the guidewire upon withdrawal of the catheter.

BRIEF DESCRIPTION OF THE DRAWINGS

FIG. 10 represents the longitudinal cross-sectional view with the polyimide tip.

FIG. 11 represents the cross-sectional view along the line 11—11 in FIG. 10.

DETAILED DESCRIPTION OF THE PREFERRED EMBODIMENTS

Figure 1:
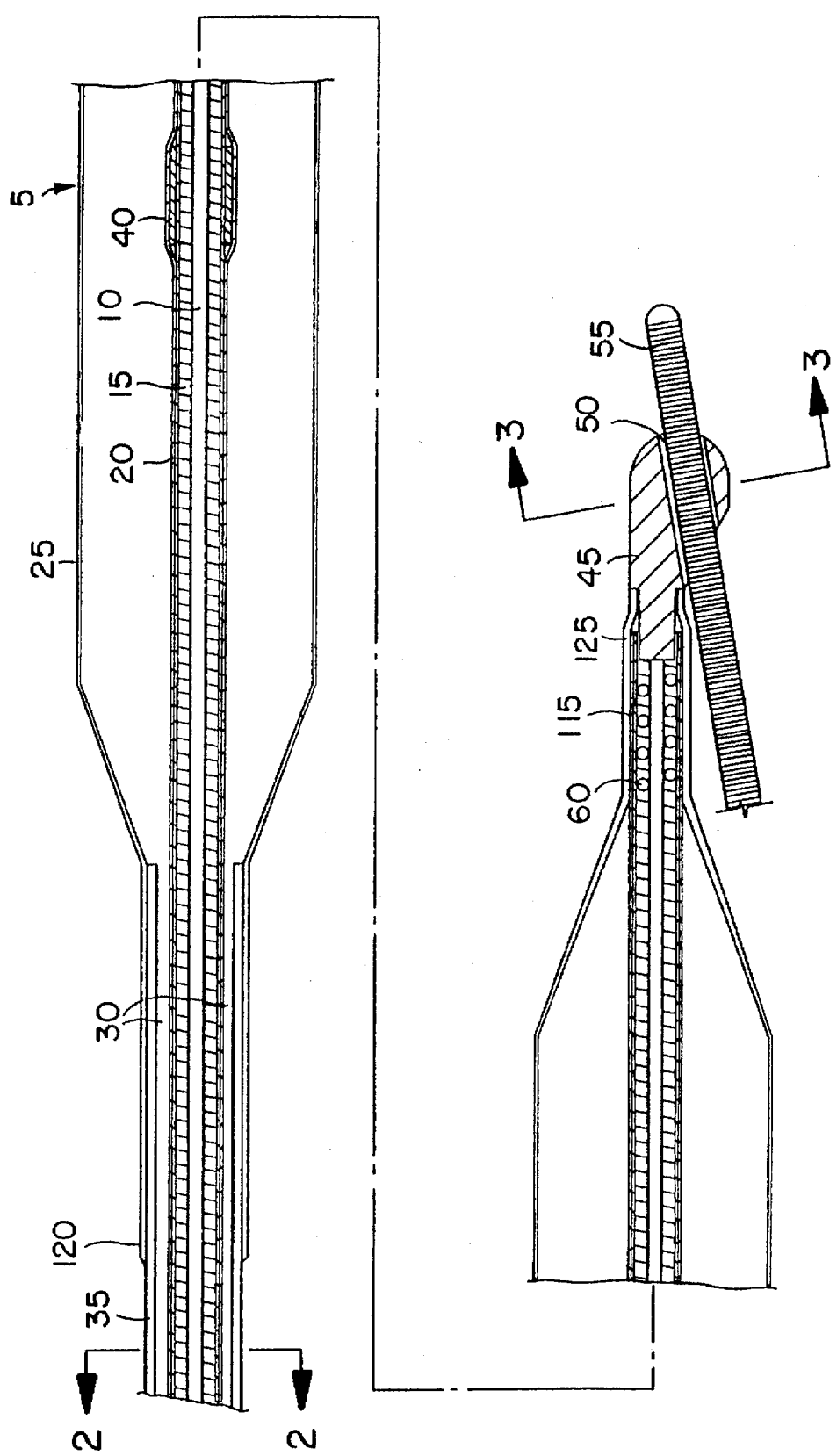
FIG. 1 represents the longitudinal cross-sectional view of a dual lumen embodiment of an angioplasty catheter incorporating the present invention.
Figure 2:
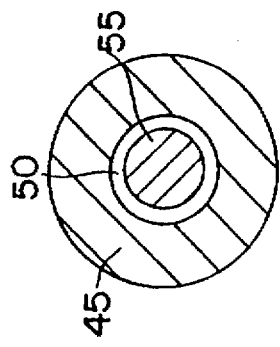
FIG. 2 represents the cross-sectional view shown in FIG. 5 along the line 2—2 of the dual lumen embodiment's region preceding the proximal end of the balloon.
Figure 3:
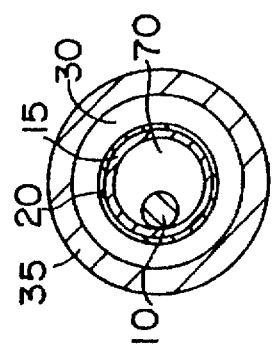
FIG. 3 represents the cross-sectional view along the line 3—3 of the dual lumen embodiment's region following the distal end of the balloon.
Figure 4:
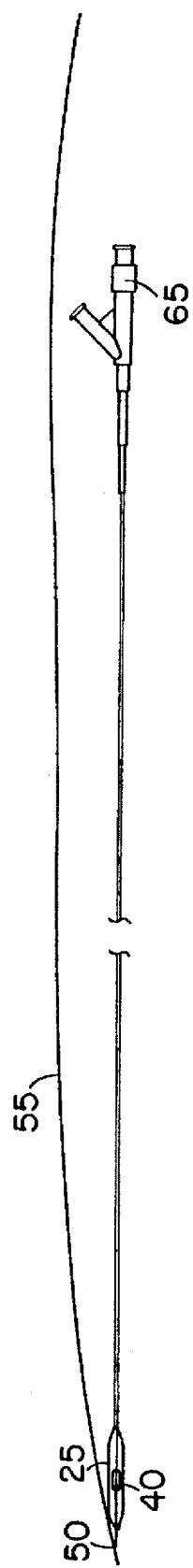
FIG. 4 represents the side elevational view of a dual lumen embodiment.

Applicants have developed a rapid exchange balloon dilatation catheter with a short tubular guidewire lumen at the distal tip. The purpose of a guidewire is to aid in positioning the catheter across a specific intervascular obstruction. This invention is intended for use as a dilatation catheter having a balloon means at the distal end to be placed across a stenosis. Under fluoroscopic guidance, the guidewire can be placed first in proximity to a stenosis and then across the stenosis. The rapid exchange balloon dilatation catheter can then be inserted into the stenosis following the path established by the guidewire. Further manipulations of the catheter are made to position the device across the obstruction. If this is successful, the balloon is inflated in such a manner that the diameter of the obstructed area is increased. In PTCA multiple catheters are frequently required during a procedure. Once a stenosis has been crossed and dilated with the dilating balloon, the dilatation catheter can be withdrawn, leaving the guidewire in position across the stenosis. A different device can then be inserted over the guidewire, as for example, an intervascular ultrasound device, an angioscopy device, a fiber optic viewing catheter, an arterial stent delivery catheter, or another dilatation catheter to further enlarge the cross sectional diameter of the obstruction by means of repeated dilatation with a balloon of greater diameter. Additionally, it may be desirable for the physician to be able to place the guidewire across another obstruction and to dilate this with a balloon dilatation catheter having a balloon of a different diameter. The average number of catheters used per patient procedure is 1.6.

The advantages of applicant's invention are first, only one operator is required for the PTCA procedure, second, an inner lumen is not required to accommodate the guidewire, third, a short exchange lumen results in less friction and a faster exchange, and fourth, pinching the guidewire is minimized as the catheter is being removed through the tortuous path thereby tending to minimize pulling out the guidewire upon withdrawal of the catheter.

With applicant's invention, only one operator is required for the procedure which does not require an inner lumen to accommodate the guidewire. In prior art the catheter is inserted over an angioplasty guidewire by inserting the guidewire into the lumen within the catheter shaft. In applicant's invention, the catheter is inserted over an angioplasty guidewire without using the lumen through the catheter shaft. The guidewire is instead back-loaded through a distal tip tubular member. A typical rapid exchange guidewire is of approximately 180 cm in length. Conventional over-the-wire methods of loading the distal end of the catheter over the proximal end of the guidewire require a lumen running throughout the catheter shaft. The conventional over-the-wire guidewire and catheter requires a guidewire length of approximately 300 cm thereby requiring two operators for the procedure.

The inner lumen in applicant's catheter shaft is not used by the guidewire and is therefore free for other uses such as blood perfusion. The inner guidewire lumen can also be eliminated entirely thereby reducing shaft profile.

A short exchange lumen causes less friction during the procedure resulting in a faster exchange. Additionally, friction between the catheter and the guidewire must be kept to a minimum to reduce extraneous movement of the guidewire and keep it stationary. The present invention addresses this matter by shortening the length of the contact surface between the catheter and the guidewire as well as by forming the exchange portion of the catheter out of a material with a very low coefficient of friction.

The present invention addresses the problem of pinching the guidewire as the catheter is being removed through the tortuous path thereby pulling out the guidewire and resulting in the loss of guidewire positioning over the stenosis. A factor which contributes to guidewire pinching includes the position of the guidewire exit port. The position of the guidewire exit port at the proximal balloon bond can cause the balloon to become snagged during withdrawal of the catheter into the ancillary guide catheter. The resultant buckling of the catheter may result in inadvertent withdrawal of the guidewire from the lesion due to seizure of the guidewire by the buckled lumen. This may have deleterious effects upon the patient undergoing angioplasty. The present invention tends to minimize the likelihood of guidewire seizure during catheter withdrawal by positioning the exchange component distal to the inflatable balloon and by using a short exchange lumen which keeps the guidewire relatively straight. A guidewire lumen of 0.75 cm can be used. Another factor which tends to minimize the likelihood of guidewire seizure in the present invention includes the low coefficient of friction in materials such as polyimide.

The distal tip guidewire lumen is a short tubular member consisting of any biocompatible material such as polyethylene, polycarbonate, polyimide, combinations thereof or biocompatible metals such as #304 stainless steel. The guidewire lumen is open on both ends and extends rearwardly (proximally) from the distal extremity of the catheter and terminates before the distal end of the balloon attachment. This tubular member allows rapid exchange of angioplasty catheters by sliding the original catheter over the guidewire and out the vessel while maintaining the position of the guidewire across the stenosis so that a new catheter can be advanced to the stenosis if required. The simple design results in lower manufacturing costs than conventional over-the-wire catheters as fewer components, fewer manufacturing steps and less tubing is required.

This invention can be implemented as either a single lumen catheter or a dual lumen catheter. The advantage of the single lumen configuration over a dual lumen configuration is that of its lower profile. A low profile enhances the ability of a catheter to cross a stenosis. The advantage of the dual lumen embodiment is that the inner lumen can be used for fluid delivery such as blood perfusion or the infusion of an oxygenated liquid, anticoagulants or other drugs.

The single lumen invention can be better understood by referring to the drawings in FIG. 5 through FIG. 8. The balloon catheter 5 single lumen system consists of the following. A central core wire 10 is made of any biocompatible material, preferably of #304 stainless steel. The core wire 10 provides stiffness which improves pushability and torquability. The core wire 10 may optionally be surrounded by a helically wound spring coil 15 which provides pushability from within instead of the need to rely on an outer shaft for pushability. The core wire 10 also provides push to the distal tip 45. The spring coil 15 can be made of any biocompatible material, preferably of #304 stainless steel. The spring coil 15 extends from the manifold 110 to the distal end of the balloon 125. The balloon 25 is made of biocompatible material such as low density polyethylene. The catheter shaft is comprised of a helical spring coil 15, which is covered by a jacket 20 consisting of a biocompatible material such as a polymer or polyethylene. The jacket 20 is heat shrunk about the spring coil 15. The distal end of the balloon 125 is heat shrunk about the distal end of the spring coil 115. The proximal end of the balloon 120 is heat shrunk about the spring coil 15. The area of the spring coil 15 within the jacket 20 defines the shaft inflation lumen 30. An aperture 100 is cut through the spring coil 15 and jacket 20 to permit transmission of fluids from the shaft inflation lumen 30 to the balloon inflation lumen 145. The core wire 10 is affixed by bonding or welding the proximal end of the core wire 10 to the spring coil 15 at the proximal end of the manifold 110. The distal end of the core wire 10 could be welded to the spring coil distal end 115. If so, however, the device would not react symmetrically since such welding will stiffen only one side. The core wire 10 is free to float within the spring coil 15 and moves independently of the spring coil 15. Balloon inflation liquids are perfused through the balloon inflation lumen 145.

A radiopaque marker band 40 is bonded to the core wire 10 preferably at the point which is the center of the balloon 25 although it could be located other places such as the proximal and/or distal ends of the balloon 25. The marker band 40 is used to provide a fluoroscopic indication of the location of the balloon 25 thereby allowing the operator to adjust the position of the balloon 25. Preferred materials for the marker band 40 include 100% gold, 100% iridium, or alloys of these materials such as a Pt-Ir alloy consisting of 90% platinum and 10% iridium. The preferred density is of at least 19.3 to 21.0 gm/cm$^3$. In an alternative or additional embodiment to the marker band 40, the entire spring coil 15, or just the distal portion of the spring coil 15 can be fabricated of a radiopaque materials as described above to make the spring coil 15 visible by fluoroscopy.

A typical one piece balloon 25 for any of applicant's embodiments has the following length, diameter and material characteristics. Balloon length ranges from 2 cm to 4 cm with the diameter size ranging from 1.5 mm to 5.0 mm. The balloon 25 is made of a biocompatible material such as low density polyethylene or similar materials which have a known diameter under a specific pressure. The distal end of the Balloon 25 is heat shrunk to the distal end of the core wire 10. Balloon 25 may also be heat shrunk over the distal tip 45 or portions thereof with the core wire 10 inserted therein and glued, bonded, brazed or fastened to the distal tip 45 with any other suitable method.

Applicant's catheter material for all embodiments comprises any biocompatible polymer or metal. Polymers include polyimide and more preferably polyethylene which is clear. A clear radiolucent material is preferable because air bubbles visible during the purging process alert the operator to malfunction. In the preferred embodiment, only the spring coil 15 and radiopaque marker band 40 are not clear.

The dual lumen invention can be better understood by referring to the drawing in FIGS. 1 through 4. The balloon catheter 5 dual lumen system consists of the following. A central core wire 10 provides stiffness which improves pushability and togrquability. The core wire 10 may optionally be surrounded by a helically wound spring coil 15 to increase pushability instead of the need to rely on an outer shaft for pushability. The core wire 10 also provides push to the distal tip 45. The spring coil 15 would, however, increase the profile and the cost and it may be more desirable to use a polymer shaft 35 instead. When a spring coil 15 is used, it extends from the manifold 65 to the distal end of the balloon 125 and is covered by a plastic jacket 20 consisting of a biocompatible material such as polyethylene which is heat shrunk about the spring coil 15. The distal end of the balloon 125 is heat shrunk to the distal end of the spring coil 115. The proximal end of the balloon 120 is heat shrunk to the shaft 35. The area of the spring coil 15 within the jacket 20 defines the inner lumen 70. The core wire 10 is free to float within the spring coil 15 and moves independently of the spring coil 15. Liquids can flow through the inner lumen 70. When this is required, one or more exit ports 60 are created in the jacket 20 and balloon distal end 125 to permit the liquid to move from the inner lumen 70 into the blood stream. A manifold 65 suitable for the introduction of additional fluids as required. A balloon inflation lumen 30 surrounds the jacket 20. The inflation lumen's 30 distal end is connected with the manifold 65 and receives liquids therethrough for purposes of inflating the balloon 25 thereby reducing the stenosis. The radiopaque marker band 40 is affixed to the spring coil 15 and can be used to fluoroscopically view the position of the balloon 25 to allow the user to adjust the position of the balloon 25. Surrounding the inflation lumen 30 is the shaft 35 which is constructed of any biocompatible material such as a polymer. The balloon 25 is affixed to the shaft 35 by heat shrinking.

Figure 5:
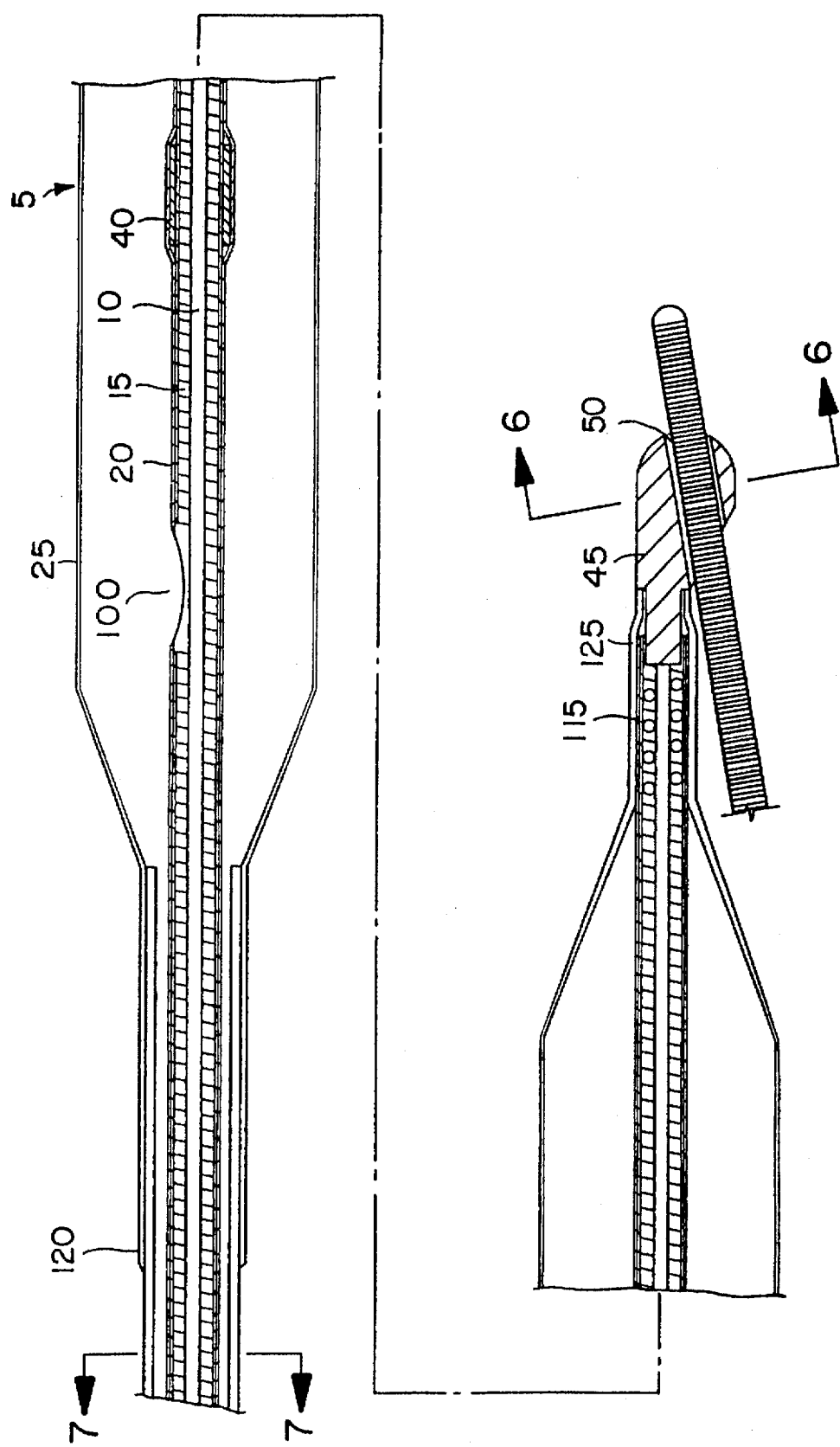
FIG. 5 represents the longitudinal cross-sectional view of a single lumen embodiment.
Figure 7:
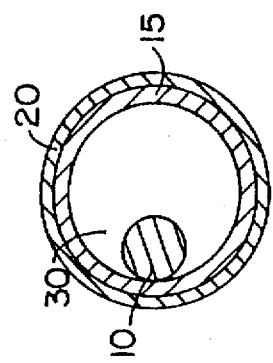
FIG. 7 represents the cross-sectional view along the line 7—7 of the single lumen embodiment's region preceding the proximal end of the balloon.
Figure 6:
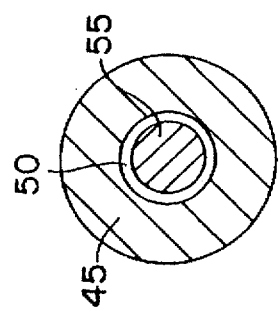
FIG. 6 represents the cross-sectional view along the line 6—6 of the single lumen embodiment's region following the distal end of the balloon.
Figure 8:
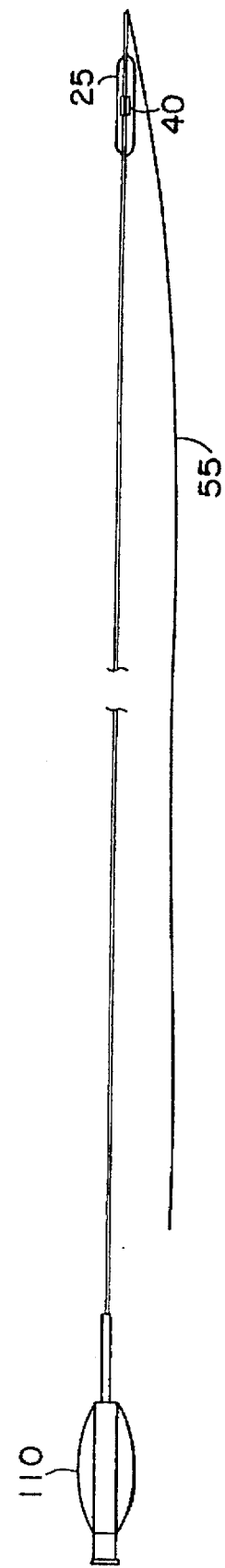
FIG. 8 represents the side elevational view of a single lumen embodiment.

For either the FIG. 1 dual lumen or the FIG. 5 single lumen embodiment the following applies. The molded distal tip 45 has a rearwardly extending guidewire lumen 50 through which the guidewire 55 is threaded. The guidewire 55 can be any useful size, preferably a standard size such as 0.010 mm, 0.014 mm, or 0.018 mm.

Figure 9A:
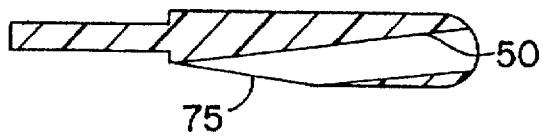
FIG. 9a represents a one piece molded tip.

The guidewire lumen 50 can be nearly parallel with the core wire 10 as a biaxial tip, or it can angle upward to the center of the distal tip 45 as in FIG. 9a. Angling the guidewire lumen 50 upward from 0 to 60 degrees, more preferably 0 to 15 degrees and most preferably 0 degrees allows a more tapered distal tip 45 with a smaller profile. The proximal end of the guidewire lumen 50 where it exits the distal tip 45 should be tapered to reduce the possibility of snagging the tapered area 75 in the guide catheter upon exit.

Figure 9B:
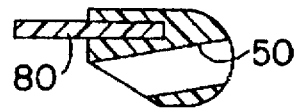
FIG. 9b represents a staked pin tip attachment.
Figure 9C:
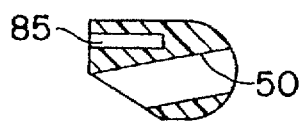
FIG. 9c represents a bored and bonded tip attachment.
Figure 9D:
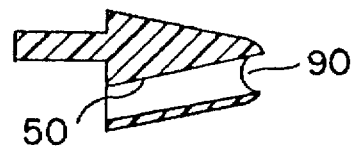
FIG. 9d represents a tip with recessed lumen.
Figure 9E:
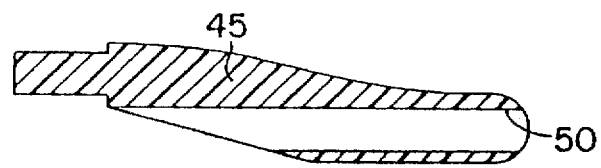
FIG. 9e represents a tip with a tubular member parallel to the shaft.

The distal tip 45 guidewire lumen 50 can be implemented with a variety of attachment variations and tip shapes. Attachment variations include bonding the distal tip 45 to the shaft 35 or a one piece molded tip as in FIG. 9a. The distal tip 45 could also be molded with a staked pin 80 and welded to the core wire 10 as in FIG. 9b. The staked pin 80 could also be threaded, knurled or ribbed for improved grip. Alternatively, as in FIG. 9c, the distal tip 45 could be bored 85 as with a laser and the distal tip 45 then fit and bonded over the distal end of the catheter shaft. Tip shape embodiments include a recess 90 for ease of loading as in FIG. 9d. The distal tip 45 could be fluted, streamlined or bullet shaped. In FIG. 9e the distal tip 45 could also exit the therapy means at a downward slope to accommodate maintaining the guidewire at a 0 degree angle to the shaft so that pinching the guidewire tends to be minimized as the catheter is removed through a tortuous path. The distal tip 45 can be implemented with a variety of shapes and attachments as long as that embodiment is capable of supporting the guidewire 55.

FIG. 10 represents a tubular embodiment member 135 of the invention with the polyimide annulus 95 in the distal tip 45. The polyimide annulus 95 acts as a reinforcement member and as a guidewire lumen 50. Polyimide is advantageous because it is stiff, absorbs force, is smooth, reduces friction, and it is strong. In addition to a polyimide, other biocompatible materials having these properties could be used. Other embodiments may include a spring coil with a polyethylene sheath. In such embodiments, the spring coil 15 does not stop at the proximal balloon bond as it does in the FIG. 10 embodiment but continues through the balloon 25. The polyimide annulus 95 should not be longer than about 0.75 cm due to the stiffness of polyimide. One example of a method of creating the polyimide annulus 95, as depicted in FIG. 10, includes the following. Cut the balloon 25 distal neck to 1 cm in length. Skive the proximal guidewire exit port 105. Insert a mandrel into a 0.25 cm to 1 cm length polyimide tube. Insert the polyimide tube into the catheter distal tip 140. Shrink the distal end of balloon 25 to capture the polyimide annulus 95. Remove the mandrel.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
| --- | --- |
| 5 | Balloon Catheter |
| 10 | Core Wire |
| 15 | Spring Coil |
| 20 | Jacket |
| 25 | Balloon |
| 30 | Shaft Inflation Lumen |
| 35 | Shaft |
| 40 | Radiopaque Marker Band |
| 45 | Distal Tip |
| 50 | Guidewire Lumen |
| 55 | Guidewire |
| 60 | Exit Port |
| 65 | Dual Lumen Manifold |
| 70 | Inner Lumen |
| 75 | Tapered Area |
| 80 | Staked Pin |
| 85 | Bore |
| 90 | Recess |
| 95 | Polyimide Annulus |
| 100 | Aperture |
| 105 | Exit Port |
| 110 | Single Lumen Manifold |
| 115 | Distal end of Spring Coil |
| 120 | Balloon Proximal End |
| 125 | Balloon Distal End |
| 130 | Distal End of Reduced Diameter |
| 135 | Tubular Member |
| 140 | Distal Tip |
| 145 | Balloon Inflation Lumen |

What is claimed is:

1. A catheter balloon and distal tip comprising:

a one piece tubular member having a proximal and distal end, the tubular member comprising a balloon, a distal end of reduced diameter and a distal tip of expanded diameter; the balloon is formed in the proximal end of the tubular member, the balloon having a proximal end and a distal end;

a core wire extending longitudinally through the balloon;

the balloon defining an inflation lumen;

the tubular member decreasing in diameter at the distal end of the balloon to form the distal end of reduced diameter, such that the tubular member makes contact with the core wire, the distal end of reduced diameter having a proximal end and a distal end, the balloon inflation lumen ending proximal to the proximal end of the distal end of reduced diameter;

the tubular member having the distal tip of expanded diameter distal to the distal end of reduced diameter, the distal tip is formed from the tubular member, the distal tip having a proximal end and a distal end, the distal end of the distal end of reduced diameter being contiguous with the proximal end of the distal tip, the distal tip defining a guidewire lumen; and a skive being cut in the proximal end of the distal tip to form a proximal port for the guidewire lumen, the guidewire lumen being sized to receive a guidewire.

2. A catheter balloon and distal tip according to claim 1, wherein the distal tip is about 0.25 cm to 1 cm in length.

3. A catheter balloon and distal tip according to claim 1, wherein the core wire extends longitudinally from the balloon through the distal end of reduced diameter and the distal tip.

* * * * *

UNITED STATES PATENT AND TRADEMARK OFFICE
CERTIFICATE OF CORRECTION

PATENT NO. : 5,667,521
DATED : September 16, 1997
INVENTOR(S) : Kenneth L. Keown It is certified that error appears in the above-identified patent and that said Letters Patent is hereby corrected as shown below:

Col. 3, Line 40:     "FIG. 5"    should be    "FIG. 1"

Col. 6, Line 57:     "togrquability"    should be    "torquability"

Signed and Sealed this

Third Day of March, 1998

Attest:

BRUCE LEHMAN

Attesting Officer      Commissioner of Patents and Trademarks